United States Patent [19]

Lin

[11] Patent Number: 5,965,759
[45] Date of Patent: Oct. 12, 1999

[54] CATALYTIC PROCESS FOR ISOMERIZING METALLOCENES

[75] Inventor: Ronny W. Lin, Baton Rouge, La.

[73] Assignee: Albemarle Corporation, Richmond, Va.

[21] Appl. No.: 09/159,528

[22] Filed: Sep. 23, 1998

[51] Int. Cl.[6] .................................. C07F 17/00; C07F 7/00
[52] U.S. Cl. ......................... 556/11; 502/103; 502/117; 526/127; 526/160; 526/943; 534/15; 556/12; 556/43; 556/53
[58] Field of Search .................................. 556/11, 12, 53, 556/43; 502/103, 117; 526/127, 160, 943; 534/15

[56] References Cited

U.S. PATENT DOCUMENTS

| | | | |
|---|---|---|---|
| 4,794,096 | 12/1988 | Ewen | 502/117 |
| 5,017,714 | 5/1991 | Welborn, Jr. | 556/12 |
| 5,036,034 | 7/1991 | Ewen | 502/117 |
| 5,145,819 | 9/1992 | Winter et al. | 502/117 |
| 5,296,434 | 3/1994 | Karl et al. | 502/117 |
| 5,324,800 | 6/1994 | Welborn, Jr. et al. | 526/160 |
| 5,329,033 | 7/1994 | Spaleck et al. | 556/53 |
| 5,455,365 | 10/1995 | Winter et al. | 556/7 |
| 5,455,366 | 10/1995 | Rohrmann et al. | 556/8 |
| 5,554,776 | 9/1996 | Langhauser et al. | 556/11 |
| 5,597,935 | 1/1997 | Jordan et al. | 556/11 |
| 5,780,660 | 7/1998 | Lin et al. | 556/11 |

FOREIGN PATENT DOCUMENTS

| | | |
|---|---|---|
| 0344887 | 12/1989 | European Pat. Off. . |
| 0574597 | 12/1993 | European Pat. Off. . |
| 0722950 | 7/1996 | European Pat. Off. . |
| 0819695 | 1/1998 | European Pat. Off. . |
| 0834514 | 4/1998 | European Pat. Off. . |
| 19525184 | 1/1997 | Germany . |
| 9619488 | 6/1996 | WIPO . |
| 9703080 | 1/1997 | WIPO . |

OTHER PUBLICATIONS

Grossman, Robert B., et al., "Enantioselective Zirconium–Mediated Synthesis of Allylic Amines", J. Am. Chem. Soc., 1991, vol. 113, pp. 2321–2322.

Wild, Ferdinand, et al., "ansa–Metallocene Derivatives. IV. Synthesis and Molecular Structures of Chiral ansa–Titanocene Derivatives with Bridged Tetrahydroindenyl Ligands", J. of Organometallic Chem., 1982, vol. 232, pp. 233–247.

Ville, G., et al., "Reversibility of n[4]–Cyclobutadiene Metal Formation from Complexed Alkynes. Unimolecular Isomerication of Labeled Racemic and Enantiomerically enriched n[5] –cyclopentakienyl–n[4]–cyclobutadiene Cobalt Complexes", ACS Symposium Series, 1982, vol. 185, pp. 285–286.

Caplus Abstract of German Patent 19525184 published Jan. 1997.

Collins, Scott et al., "Synthesis of Pure Racemic Isomers of ansa–Titanocene Dichlorides: Conformational Preferences are Determined by Substitution Patterns On the Cyclopentadienyl Rings", Organometallics, vol. 10, 1991, pp. 2349–2356.

Huhn, Thomas et al., "Efficient Preparation of Racemic Isomers of ansa–Zirconocene Complexes with a Vinyl Substituted Silylene Bridge", Chemistry Letters, 1997, pp. 1201–1202.

Schmidt, Katrin et al., "Photochemical Isomerization of $Me_2$ Si–Bridged Zirconocene Complexes. Application to Steroselective Syntheses of ansa–Zirconocene Binaphtholate Steroisomers", Organometallics, 1997, vol. 16, pp. 1724–1728.

Ville, G. et al., "On the Reversibility of n4–Cyclobutadiene–Metal Formation From Complexed Alkynes: Unimolecular Isomerization of Labeled Racemic and Enantiomerically Enriched n5–Cyclopentalienyl–n4–cyclobutadiene–Cobalt Complexes", J. Am. Chem. Soc., 1981, vol. 103, pp. 5267–5269.

Primary Examiner—Porfirio Nazario-Gonzalez
Attorney, Agent, or Firm—Philip M. Pippenger

[57] ABSTRACT

It has been discovered that the meso form of metallocenes can be catalytically isomerized to the racemic form of the metallocene. This is accomplished by heating an isomerization mixture formed from (i) a meso form of a bridged metallocene or a mixture of meso and racemic forms of a bridged metallocene, (ii) a Group 1 and/or 2 metal halide isomerization catalyst, and (iii) a liquid organic isomerization medium, such that at least a portion of the meso form of the metallocene is isomerized to the racemic form.

30 Claims, No Drawings

1

CATALYTIC PROCESS FOR ISOMERIZING METALLOCENES

TECHNICAL FIELD

This invention relates to processing of meso or mixtures of meso and racemic forms of metallocenes so as to convert at least a portion of the meso form to the racemic form. More particularly, this invention relates to the discovery that it is possible to catalytically isomerize meso or mixtures of meso and racemic forms of metallocenes into products in which the content of the racemic form is substantially increased.

BACKGROUND

Chiral metallocenes are useful for the synthesis of polyolefins. The racemic form of these metallocenes provides stereoregular polymers, e.g., poly(alpha-olefins). In addition, racemic metallocenes are considerably more active as catalysts than the meso metallocenes, which tend to produce only low molecular weight atactic polymers. Metallocenes and their use as catalysts in forming various olefin polymers are described, for example, in U. S. Pat. Nos. 4,794,096; 5,017,714; 5,036,034; 5,145,819; 5,296,434; 5,324,800; 5,329,033; 5,455,365; and 5,455,366, the full disclosures of which are incorporated herein by reference.

Processes for the synthesis of such metallocenes tend to form mixtures of the meso and racemic forms. One way of obtaining the racemic metallocene is to carry out a physical separation of the racemic and meso forms in such mixtures. For example use can be made of crystallization or extraction procedures such as described in EP 344 887, or Huhn, et al., *Chem. Lett.,* 1997, 12, 1201–1202; or by chromatographic procedures such as described by Wild, et al., *J. Organomet. Chem.,* 1982, 232, 233–247 or by Grossman, et al., *J. Am. Chem. Soc.,* 1991, 113, 2321–2322. However such procedures are not well suited for use on an industrial scale because of their expense and low yield.

Other methods for separating the racemic and meso metallocene forms have been proposed. Thus EP 819 695 (published Jan. 21, 1998) describes modifying the racemic/meso ratio of a racemic/meso mixture of a stereorigid, bridged metallocene by subjecting the mixture to selective decomposition of the undesired isomer in the presence of compounds having either acidic hydrogen atoms reactive halogen atoms, such as water, methanol, ethanol, acetic acid, hydrochloric acid, chlorotrimethylsilane, or p-toluenesulfonic acid. For example, use of water with a 1:1 mixture of rac/meso 1,2-ethylene bis(4,7-dimethylindenyl) zirconium dichloride gave 100% of the meso form, and thus destroyed the racemic form.

Another approach involves photochemical isomerization procedures. Thus DE 19,525,178, DE 19,525,184, WO 97/03080, and Schmidt, et al., *Organometallics,* 1997, 16(8), 1724–1728 describe procedures involving irradiation of meso metallocenes or rac/meso metallocene mixtures into racemic forms in the presence of a chiral reagent such as the R(+) enantiomer of dilithium binaphtholate.

It would be most advantageous if a way could be found for effectively treating meso metallocenes or mixtures of meso and racemic metallocenes so as to produce a product enriched in the desirable racemic form without use of extraction, crystallization, or chromatographic separations, without destruction of one of the isomeric forms, and without need for use of photolysis apparatus and chiral reagents.

U.S. Pat. No. 5,780,660 (issued Jul. 14, 1998) describes an isomerization process in which a slurry of (i) a mixture of meso and racemic forms of a bridged zirconocene in (ii) a liquid ether-containing isomerization medium, is maintaining at one or more temperatures, preferably 30 to 70° C., for a period of time such that a racemate enriched zirconocene is formed.

THE INVENTION

This invention makes it possible to perform catalytic isomerizations of metallocenes. Moreover, the catalytic process of this invention is superior to the zirconocene isomerization process described in U.S. Pat. No. 5,780,660, supra. Indeed, the process of this invention is deemed capable of converting or transforming meso or mixtures of meso and racemic metallocenes of transition, lanthanide or actinide metals into products enriched in the desired racemic forms, all without need for photolysis or use of ancillary chiral reagents, and without selective destruction of one form or the other.

Pursuant to this invention an isomerization process is provided which comprises heating an isomerization mixture formed from (i) a meso form of a bridged metallocene or a mixture of meso and racemic forms of a bridged metallocene, (ii) a Group 1 or 2 metal halide isomerization catalyst, and (iii) a liquid organic isomerization medium, such that at least a portion of the meso form of the metallocene is isomerized to the racemic form.

There are various ways of conducting this process. In one embodiment of this invention, a slurry is produced by combining the mixture of meso or meso and racemic metallocene, the Group 1 or 2 metal halide, and the liquid isomerization medium in proportions such that a slurry is formed in the isomerization medium, and the resultant slurry is maintained at or subjected to at least one suitable isomerization temperature. In another embodiment, the slurry is produced by combining the meso or meso and racemic metallocenes, the Group 1 or 2 metal halide, and the liquid isomerization medium in proportions such that at least the metallocene substantially completely dissolves in the isomerization medium. The resultant metallocene solution is concentrated (e.g., by vacuum evaporation of isomerization medium) such that a solids phase appears in the isomerization medium. Depending upon the temperature(s) used in the concentration step and length of time the mixture is maintained at such temperature(s), continued or subsequent heating of the slurry without further removal of isomerization medium may be used to effect isomerization or more isomerization of meso to racemic metallocene. In still another embodiment all of the isomerization medium can be removed from the slurry (e.g., by vacuum evaporation of all of the isomerization medium). Depending upon the temperature(s) used in removing the isomerization medium and length of time the mixture is maintained at such temperature(s), the resultant metallocene may again be mixed with isomerization medium and Group 1 or 2 halide isomerization catalyst, and the resultant mixture subjected to one or more isomerization temperatures for a period of time long enough to achieve the desired extent of conversion of meso form to racemic forms of the metallocene.

In each of the embodiments of this invention the liquid organic isomerization medium is preferably an ether-containing medium. In other words the medium can be one or more ethers, or it can be mixture of one or more ethers with one or more other suitable organic diluents or solvents, such as a hydrocarbon solvent or diluent.

In the metallocene systems studied to date, the racemic form of the metallocene has been found to be less soluble in a liquid ether medium than the meso form of the metallocene. Thus not only does this solubility difference keep more of the meso isomer in solution where it can be isomerized, but in addition the less soluble racemic form tends to precipitate out as a solids phase during the course of the isomerization. This in turn makes it possible during the isomerization period for additional meso isomer to progressively dissolve in the ether medium as the racemic form is progressively coming out of solution. And because the desired racemic form is in the solids phase, it is readily recovered from the liquid phase by conventional procedures such as decantation, centrifugation or filtration.

The process of this invention should not be confused with procedures where one or other of the meso or racemic forms of a metallocene is selectively extracted away from the other by virtue of a difference in solubility. In the present invention there is a molecular transformation of the meso form into the racemic forms of the metallocene. Such transformation can readily be perceived by use of NMR analyses of both the isomerized metallocene product and the isomerization medium in which the metallocene product was isomerized. It will be seen that the amount of the metallocene racemate in the product will exceed the amount initially present in the metallocene, and conversely that the amount of meso metallocene, if any, in the metallocene product and isomerization medium will be less than present in the initial metallocene.

Typically the isomerization is performed in the presence of an isomerization catalyst at one or more temperatures in the range of about 30° C. to about 120° C., and preferably in the range of about 40° C. to about 90° C. The rate of isomerization tends to vary with temperature and thus is usually more rapid at higher temperatures and less rapid at lower temperatures. Accordingly, the isomerization reaction is performed for a period of time sufficient under the conditions employed to achieve a suitable or desired amount of isomerization. Typically isomerization periods fall in the range of about 0.5 to about 48 hours. With isomerization temperatures in the range of about 40 to about 90° C., periods in the range of about 1 to about 24 hours are preferred. As in U.S. Pat. No. 5,780,660 the temperature of the isomerization mixture can be (but need not be) raised and lowered on at least two separate occasions (most preferably using at least three up and down cycles) during the course of the isomerization operation, with each of the changes in temperature, whether up or down, amounting to at least 15° C., while keeping the temperature within the overall isomerization temperature range. For example, if raising and lowering the temperature on two separate occasions, the temperature may first be raised to, say, 60° C. and then lowered to, say, 30° C., and then raised to say, 65° C., and then lowered to, say, 50° C.

It is desirable to agitate the isomerization mixture during at least a substantial portion of the isomerization reaction period.

In carrying out the process of this invention it is desirable, and thus preferred, that at least 10% of the meso form in the initial metallocene be converted to the racemic form of the metallocene. However, depending upon the makeup of the initial metallocene a greater or lesser amount of such isomerization can be effected, and in any event is beneficial.

Metallocenes suitable for use in the practice of this invention can be represented by the formula:

$$QCp_2MR_n$$

where Cp independently in each occurrence is a cyclopentadienyl-moiety-containing group which typically has in the range of 5 to about 24 carbon atoms, with the proviso that the two Cp groups are of such configuration that a meso form as well as a racemic form of the metallocene exists; Q is a bridging group or ansa group that links the two Cp groups together; M is transition, lanthanide, or actinide metal atom; each R is independently a group that is sigma-bonded to the metal atom, M; and n is a whole integer from 1 to 3, preferably 2. The sum of 2+n is sufficient to form a stable compound, and often is the coordination number of the metal atom, M, and thus 2+n is usually from 3 to 5. When M is a Group 4 metal or an actinide metal, n is 2. When M is a Group 3 or Lanthanide metal, n is typically 1. When M is a Group 5 metal, n is typically 3.

A metallocene that has a plane of symmetry through the metal atom and the Cp rings (meso form) and that cannot be rotated 180° into a configuration not having a plane of symmetry (racemic form) is achiral, and is not used in the practice of this invention. Used in this invention is (i) a chiral metallocene in meso form that can be rotated 180° into the racemic form not having a plane of symmetry, or (ii) a chiral metallocene mixture composed in part of the racemic form, and in part of the meso form capable of being rotated 180° into the racemic form.

Preferably, the Cp groups are cyclopentadienyl groups, indenyl groups, fluorenyl groups, or related groups that can bond, typically via π-bonding, to the metal. These groups can be substituted or unsubstituted provided that the resultant metallocene is a chiral metallocene as opposed to an achiral metallocene. Among the substituents that can be present are hydrocarbyl, hydrocarbyloxy, halo, halohydrocarbyl, heteroaromatic, hydrocarbyl-metalloid, and/or halohydrocarbylmetalloid groups. Adjacent carbon atoms of the Cp group can be substituted by a two separate carbon atoms of a substituent group that thereby creates a ring fused onto the Cp group. The Cp groups often have, but need not have, at least one methyl substituent on the cyclopentadienyl ring portion of the Cp group. Other hydrocarbyl substituents which may be present on the ring or rings of Cp in addition to or in lieu of one or more methyl groups include $C_2$ or higher alkyl, aryl, aralkyl, cycloalkyl, cycloalkylcarbinyl, or other similar monovalent substituents. Cp typically contains up to 75 non-hydrogen atoms. Q is typically a silanediyl ($R_2Si<$) (also known as a silanylene, silylene, or silyl group), germanediyl ($R_2Ge<$), benzo ($C_6H_4<$), substituted benzo, methylene (—$CH_2$—), substituted methylene ($R_2C<$ or HRC<), ethylene (—$CH_2CH_2$—), or substituted ethylene bridge. Other bridging groups have also been proposed, such as—SiO—, —Si—O—C—, —Si—O—Si—, and bridging groups comprising tin. M is preferably a metal atom of Groups 4–6, and most preferably is a Group 4 metal atom, especially hafnium, and most especially zirconium. R is, independently, typically a halogen atom (Cl, Br, I), a hydrocarbyl group (alkyl, cycloalkyl, alkenyl, cycloalkenyl, aryl, aralkyl, etc.), a halohydrocarbyl group, a hydrogen atom, an amido group, triflate, a hydrocarbyloxy group or any other monovalent group that forms a stable metallocene when bonded to the metal atom, M. R can be a divalent substituent such as an alkylidene group, a cyclometallated hydrocarbyl group, or any other divalent chelating ligand, two loci of which are singly bonded to M to form a cyclic moiety which includes M as a member.

Preferably, n is 2 and each R is a halogen atom or a hydrocarbyl group, and most preferably the two R groups will be the same, e.g., two chloro groups, two methyl groups, two ethyl groups, or two phenyl groups, or analogous univalent substituents.

Non-limiting examples of metallocenes to which this invention is applicable include such compounds as:

[ethylenebis(2-methyl-1-cyclopentadienyl)]titanium dichloride;
[ethylene(2-methyl-1-cyclopentadienyl)(2-isopropyl-1-cyclopentadienyl)]titanium dichloride;
[ethylene(2-methyl-1-cyclopentadienyl)(2-tert-butyl-1-cyclopentadienyl)]titanium dichloride;
[ethylenebis(methylcyclopentadienyl)]titanium dimethyl;
[dimethylsilanediylbis(2-methylcyclopentadienyl)] zirconium dichloride;
[dimethylsilanediylbis(indenyl)]zirconium dichloride;
[dimethylsilanediylbis(2-methylindenyl)]zirconium dichloride;
[dimethylsilanediylbis(4,5,6,7-tetrahydroindenyl)] zirconium dichloride;
[dimethylsilanediylbis(2-methyl4-tert-butylcyclopentadienyl)]zirconium dichloride;
[dimethylsilanediylbis(2-methyl-4-phenylcyclopentadienyl)]zirconium dichloride;
[dimethylsilanediylbis(4,5-dibenzo-2-methylindenyl)] zirconium dichloride;
[dimethylsilanediylbis(2-methyl-4-phenylindenyl)] zirconium dichloride;
[dimethylsilanediylbis(7-methoxy-4-phenylindenyl)] zirconium dichloride;
{dimethylsilanediylbis[4,5-(4',5'-acenaphtho)indenyl]}zirconium dichloride;
[dimethylsilanediylbis(2-methyl4-naphthylindenyl)] zirconium dichloride;
[(methyl)(vinyl)silanediylbis(2,4-dimethylcyclopentadienyl)]zirconium dichloride;
[di(vinyl)silanediylbis(2,4-dimethylcyclopentadienyl)] zirconium dichloride;
[ethylenebis(ethylcyclopentadienyl)]zirconium dichloride;
[ethylenebis(indenyl)]zirconium dichloride;
[ethylenebis(4,7-dimethylindenyl)]zirconium dichloride;
[ethylenebis-7,7'-(2-methylindenyl)]zirconium dichloride;
[ethylenebis-7,7'-(2,4-dimethylindenyl)]zirconium dichloride;
[ethylenebis-7,7'-(4-methylindenyl)]zirconium dichloride;
[2,2-propylidene(2,4-dimethylcyclopentadienyl)(indenyl)] zirconium dichloride;
[dimethylsilanediylbis(2,4-trimethylsilanylcyclopentadienyl)]hafnium dichloride;
[dimethylsilanediylbis(2-trimethylsilanylcyclopentadienyl)] hafnium dimethyl;
[dimethylsilanediylbis(indenyl)]hafnium dichloride;
[dimethylsilanediylbis(indenyl)]hafnium dimethyl;
[dimethylsilanediylbis(2-methyl-4-phenylindenyl)]hafnium dichloride;
[dimethylsilanediylbis(2-methyl-4-phenylindenyl)]hafnium dimethyl;
[dimethylsilanediylbis(2-methyl-4-phenylindenyl)]hafnium diphenyl;
[dimethylsilanediylbis(4,5,6,7-tetrahydroindenyl)]hafnium dichloride;
[dimethylsilanediylbis(4,5,6,7-tetrahydroindenyl)]hafnium dimethyl;
[dimethylsilanediylbis(indenyl)]scandium chloride; and
[dimethylsilanediylbis(indenyl)]scandium methyl.

Preferred starting materials are the meso form or mixtures of the racemic and meso forms of 1,1'-dihydrocarbylsilanediyl-bridged zirconocenes, and more preferred are [1,1'-dimethylsilanediylbis(indenyl)] zirconium dihalides wherein, optionally, either or both of the indenyl groups is/are substituted by one or more alkyl and/or aryl groups.

Isomerization catalysts which may be used pursuant to this invention are one or more Group 1, one or more Group 2, or one or more Group 1 together with one or more Group 2 metal halides. Thus use can be made of one or a combination of two or more of the catalytic monohalides selected from lithium, sodium, potassium, rubidium, or cesium monohalides; or a catalytic combination of one or a combination of two or more monohalides of lithium, sodium, potassium, rubidium, or cesium. Likewise use can be made of one or a combination of two or more of the catalytic dihalides selected from beryllium, magnesium, calcium, strontium, or barium dihalides; or a catalytic combination of one or more of the Group 1 metal monohalides with one or more of the Group 2 metal dihalides. The foregoing salts are preferably used in anhydrous condition. Of the foregoing catalytic salts, lithium monohalides and magnesium dihalides are preferred. Of these, LiCl, LiBr and $MgCl_2$ are at present the more preferred catalysts, with LiCl and LiBr being the most active and therefore the most preferred catalysts tested to date.

Various liquid solvent/diluents can be used as isomerization media in the practice of this invention. Preferred are ethers. However, other solvent/diluents that do not materially inhibit, prevent or otherwise interfere with the catalytic isomerization process of this invention may be used.

Ethers used in forming the isomerization medium preferably comprise cyclic and acyclic monoethers and polyethers that exist in the liquid state at, and preferably below, the lowest isomerization temperature to be used in the particular isomerization operation being conducted. However it is possible to employ ethers which exist in the solid state at the lowest isomerization temperature being used, provided such ethers are used in admixture with an additional inert liquid solvent such as a liquid hydrocarbon or a liquid tertiary amine in which the ether is soluble at the lowest isomerization temperature, so as to thereby provide a continuous liquid phase in which the isomerization is to be performed.

Typical ethers which may be used include acyclic ethers, such as dialkyl ethers, dialkenylethers, dicycloalkyl ethers, diaryl ethers, diaralkyl ethers, alkyl-arylethers, alkylcycloalkyl ethers, etc.; dialkylethers of diols such as dialkylethers of such diols as ethylene glycol, propylene glycol, 1,4-butanediol, etc.; trialkylethers of triols such as trialkylethers of glycerine, etc., dialkylethers of diethylene glycol; dialkylethers of triethylene glycol; dialkylethers of tetraethylene glycol; tetraalkylethers of pentaerythritol, and similar liquid acyclic ethers. Also preferred for use in forming the isomerization medium are cyclic ethers having at least 5-membered rings, and polyethers, such as 1,2-dimethoxyethane, methoxyethylether, and similar liquid acyclic polyethers, tetrahydrofuran, 2,3-benzofuran, alkyldihydrofurans, alkyltetrahydrofurans, alkyltetrahydrofurfuryl ethers, alkyldihydropyrans, tetrahydropyran, 1,4-dioxane, 1,3-dioxolane, and similar liquid cyclic ethers. When another type of inert solvent (e.g., an inert liquid hydrocarbon solvent, a liquid tertiary amine, a liquid mixture of hydrocarbon and tertiary amine, or the like) is used in combination with one or more ethers to form the isomerization medium, the resultant liquid medium preferably contains at least about 70% by volume, more preferably at least 80% and most preferably at least 90% by volume of the ether(s).

The solvents used can have at least some influence on the efficiency of the isomerization. For example it has been found that 1,2-dimethoxyethane is a better isomerization medium than tetrahydrofuran for isomerizing meso-[1,1'-dimethylsilanediylbis(2-methyl-4-phenylindenyl)] zirconium dichloride (as a rac/meso mixture) to rac-[1,1'-dimethylsilanediylbis(2-methyl-4-phenylindenyl)]

zirconium dichloride. On the other hand, tetrahydrofuran is a better isomerization medium than 1,2-dimethoxyethane for isomerizing meso-[1,1'-dimethylsilanediylbis(2-methyl-4-phenylindenyl)]zirconium dimethyl (as a rac/meso mixture) to predominantly rac-[1,1'-dimethylsilanediylbis(2-methyl-4-phenylindenyl)]zirconium dimethyl.

The isomerization of meso to racemic metallocenes pursuant to this invention can be conducted with the metallocene initially either in solution or in the form of a slurry in the ether-containing solvent/diluent. Thus, although somewhat less efficient, it is possible to heat up a mixture of the isomerizable metallocene and the solvent/diluent such that all of the metallocene dissolves. After sufficient time for the isomerization in solution to take place, the solution can then be cooled so that one of the forms of the metallocene comes out of solution as a precipitate. In many cases the precipitate will be the racemic form of the metallocene. However, in some cases the precipitate may be the meso form. In either event the reduction in temperature with consequent solids formation facilitates separation as between the meso and racemic forms after the isomerization has been carried out. Preferably however, the isomerizable metallocene is initially present in the solvent/diluent in slurry form, as this enables a more efficient isomerization/separation operation. Accordingly, in this preferred mode of operation, the proportions as between the ether-containing liquid phase and the meso or mixture of meso and racemic metallocenes is such as to form a slurry wherein a portion of the metallocene is in solution and a portion of the metallocene is in the form of solid particles in the continuous liquid phase. For efficient operation the proportions used will typically be such as to provide a slurry wherein the liquid phase contains an amount of solid particles falling in the range of about 3 to about 50 wt %, and preferably in the range of about 6 to about 35 wt %.

The manner by which the initial mixture of meso and racemic metallocene isomers is produced or formed is not critical. Likewise, the manner by which the isomerization catalyst is introduced into, or even formed in situ in, the isomerization mixture is not critical. What is important is that the initial mixture be amenable to catalytic isomerization pursuant to this invention such that the racemic isomer content of the metallocene can be increased by conversion of its meso isomer in accordance with the practice of this invention.

A number of suitable methods exist for preparing the initial isomerizable metallocenes, and such methods can be found in the literature. Among such desirable synthesis methods are those set forth for example, by Spaleck, W., et al., *Organometallics*, 1994, 13, 954–963.

The practice and advantages of this invention are demonstrated by the following examples which are presented for purposes of illustration and not limitation. In these Examples "rac" is used as an abbreviation for racemic. All values are by weight unless otherwise specified. Determination of rac/meso ratios were accomplished by use of NMR.

Comparative Example A $MeCl_2$ (70 g) was used to dissolve [1,1'-dimethylsilanediyl-bis(2-methyl-4-phenylindenyl)]zirconium dichloride from its crude solid (3.56 g with rac/meso ratio of 56/44). Undissolved solid impurities were filtered off. The resultant solution was concentrated and DME (1,2-dimethoxyethane; 9.0g) was added. The slurry was heated up to 54° C. to strip off more $MeCl_2$ solvent, and the slurry was stirred at about 51–54° C. for about 3 hours. A sample taken at this point had a rac/meso ratio of 58/42. Additional riding at about 54–58° C. for approximately 5.5 hours resulted a rac/meso ratio of 60/40.

It can be seen from Comparative Example A that the combination of an ether solvent and thermal energy did cause some isomerization but the isomerization was quite slow.

EXAMPLE 1

LiCl (0.10 g) was added to the final slurry of Example A. The mixture was heated up and stirred at approximately 59° C. for about 8 hours. The rac/meso ratio of the metallocene in the slurry was substantially improved to 98.7/1.3.

EXAMPLE 2

$MgCl_2$ (about 0.03 g) was added to a slurry of [1,1'-dimethylsilanediyl-bis(2-methyl- 4-phenylindenyl)]zirconium dichloride (0.50 g; a product with a rac/meso ratio of 59.4/40.6) in DME (2.0 g). The slurry was stirred at about 59° C. for 6 hours. The rac/meso ratio of the metallocene was increased to 68.5/31.5.

EXAMPLE 3

To the final slurry of Example 2, more [1,1'-dimethylsilanediyl-bis(2-methyl4-phenylindenyl)]zirconium dichloride (0.95 g of the same feed as used in Example 2 with a rac/meso ratio of 59.4/40.6), more DME (4.0 g) and LiCl (0.03 g) were added. The slurry was stirred at about 59–63° C. for about 7 hours. Analysis of a sample of the resulting slurry showed that the metallocene had a rac/meso ratio of 99.1/0.9. After filtration, washing and drying, a solid metallocene product (1.42 g) was obtained with about 98.3 wt % racemate and about 0.2 wt % meso isomer (rac/meso ratio of 99.8/0.2). The yield was about 97%. By way of comparison, when the zirconocene (rac/meso of about 60/40) was crystallized with methylene dichloride solvent, the yield of the rac isomer was only about 10%.

Comparative Example B

A purified [1,1'-dimethylsilanediyl-bis(2-methyl4-phenylindenyl)]zirconium dimethyl (about 0.93 g) was slurried in THF (8.0 g). The slurry (in which the metallocene had a rac/meso ratio of 56.3/43.7) was heated up and stirred at about 55–57° C. Samples taken at 2.5 and 6 hours showed on analysis that the metallocene had rac/meso ratios of 57.6/42.4 and 59.3/40.7, respectively.

EXAMPLE 4

A portion (2.98 g) of the slurry from Comparative Example B (rac/meso ratio of 59.3/40.7) was transferred to a small flask. LiCl (about 0.02 g) was added. The slurry was heated up to and caused to ride at about 55–57° C. Analysis of samples taken at 3 and 6 hours showed that the metallocene had rac/meso ratios of 82.8/17.2 and 86.5/13.5, respectively.

EXAMPLE 5

$MgCl_2$ (about 0.03 g) was added to the slurry (2.35 g) from Comparative Example B having a rac/meso ratio of 59.3/40.7. The slurry was heated up and held at 55–56° C. After 3 hours, the rac/meso ratio of the metallocene changed from 59.3/40.7 to 67.1/32.9.

EXAMPLE 6

LiBr (about 0.03 g) was added to a slurry of [1,1'-dimethylsilanediyl-bis(2-methyl4-phenylindenyl)]

zirconium dimethyl (about 2.7 g; with a rac/meso ratio of 61.8/38.4) in THF. Riding the slurry at about 56–57° C. for about 3 hours improved the ratio of the metallocene to 77.6/22.4.

Comparative Example C

A purified rac/meso-[1,1'-dimethylsilanediylbis(2-methyl-4-phenylindenyl)]hafnium dichloride (0.5 g) was slurried in DME (2.3 g). The slurry was heated to and maintained at about 53–55° C. for 6 hours. After the slurry cooled to about room temperature a sample was taken for analysis. The sample was found to have a rac/meso ratio of 67.3/32.7 as compared to a rac/meso ratio of 64.6/35.4 for the original hafnocene.

EXAMPLE 7

LiCl (0.02 g) was added to the slurry remaining from Example C above. The slurry was heated to and held at about 53–55° C. for 6 hours, and then allowed to cool. Analysis of the resultant slurry showed the rac/meso ratio of the [1,1'-dimethylsilanediylbis(2-methyl-4-phenylindenyl)]hafnium dichloride had been substantially increased to 97.9/2.1. Workup provided 0.41 g of the racemic hafnocene in almost a quantitative yield.

The materials referred to by chemical name or formula anywhere in the specification or claims hereof are identified as ingredients to be brought together in connection with performing a desired operation or in forming a mixture to be used in conducting a desired operation. Accordingly, even though the claims hereinafter may refer to substances in the present tense ("comprises", "is", etc.), the reference is to the substance, as it existed at the time just before it was first contacted, blended or mixed with one or more other substances in accordance with the present disclosure. The fact that a substance may lose its original identity through a chemical reaction, complex formation, solvation, ionization, or other transformation during the course of contacting, blending or mixing operations, if done in accordance with the disclosure hereof and with the use of ordinary skill of a chemist and common sense, is within the purview and scope of this invention.

Each and every patent or other publication referred to in any portion of this specification is incorporated in full into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A metallocene isomerization process which comprises heating an isomerization mixture formed from (i) a meso form of a bridged metallocene or a mixture of meso and racemic forms of a bridged metallocene, (ii) a Group 1 and/or 2 metal halide isomerization catalyst, and (iii) a liquid organic isomerization medium, such that at least a portion of the meso form of the metallocene is isomerized to the racemic form.

2. A process according to claim 1 wherein the organic isomerization medium is an ether-containing medium.

3. A process according to claim 1 wherein the metal halide used in forming the isomerization mixture is a lithium halide.

4. A process according to claim 1 wherein the metal halide used in forming the isomerization mixture is a magnesium halide.

5. A process according to claim 1 wherein the metal halide used in forming the isomerization mixture is lithium chloride.

6. A process according to claim 1 wherein the metal halide used in forming the isomerization mixture is lithium bromide.

7. A process according to claim 1 wherein the metal halide used in forming the isomerization mixture is magnesium chloride.

8. A process according to claim 1 wherein the metallocene used in forming the isomerization mixture is a chiral metallocene of a Group 4, 5, or 6 metal.

9. A process according to claim 1 wherein the metallocene used in forming the isomerization mixture is a chiral metallocene of a Group 4 metal.

10. A process according to claim 1 wherein the metallocene used in forming the isomerization mixture is a chiral metallocene of zirconium.

11. A process according to claim 1 wherein the metallocene used in forming the isomerization mixture is a chiral metallocene of hafnium.

12. A process according to claim 1 wherein the metallocene used in forming the isomerization mixture is a chiral 1,1'-dihydrocarbylsilanediyl-bridged metallocene of a Group 4 metal.

13. A process according to claim 12 wherein the Group 4 metal is zirconium.

14. A process according to claim 12 wherein the Group 4 metal is hafnium.

15. A process according to claim 1 wherein the organic isomerization medium is an ether-containing medium, wherein the metal halide used in forming the isomerization mixture is a lithium halide, and wherein the metallocene used in forming the isomerization mixture is a chiral metallocene of a Group 4, 5, or 6 metal.

16. A process according to claim 1 wherein the organic isomerization medium is an ether-containing medium, wherein the metal halide used in forming the isomerization mixture is lithium chloride or lithium bromide, and wherein the metallocene used in forming the isomerization mixture is a chiral metallocene of a Group 4 metal.

17. A process according to claim 16 wherein the metallocene used in forming the isomerization mixture is a chiral metallocene of zirconium.

18. A process according to claim 16 wherein the metallocene used in forming the isomerization mixture is a chiral metallocene of hafnium.

19. A process for the preparation of a chiral metallocene wherein a reaction product mixture is produced that comprises racemic and meso forms of a chiral metallocene of a transition, lanthanide or actinide metal in a liquid organic reaction medium; wherein a Group 1 or 2 metal halide isomerization catalyst is introduced into said mixture; and wherein the resultant mixture is heated such that at least 10% of the meso form of the metallocene is isomerized to the racemic form.

20. The process of claim 19 wherein at least one liquid ether is present in said resultant mixture.

21. The process of claim 19 further comprising introducing (a) at least one liquid cyclic ether or (b) at least one acyclic polyether, or both of (a) and (b), into said resultant mixture before or during the heating thereof.

22. The process of claim 19 wherein the chiral metallocene in said reaction product mixture comprises the racemic and meso forms of a chiral metallocene of a Group 4, 5, or 6 metal.

23. The process of claim 19 wherein the chiral metallocene in said reaction product mixture comprises the racemic and meso forms of a chiral metallocene of a Group 4 metal.

24. The process of claim 19 wherein the chiral metallocene in said reaction product mixture comprises the racemic and meso forms of a chiral metallocene of zirconium.

25. The process of claim 19 wherein the chiral metallocene in said reaction product mixture comprises the racemic and meso forms of a chiral 1,1'-dihydrocarbylsilanediyl-bridged metallocene of a Group 4 metal.

26. The process of claim 25 wherein the Group 4 metal of said chiral 1,1'-dihydrocarbylsilanediyl-bridged metallocene is zirconium.

27. The process of claim 25 wherein the Group 4 metal of said chiral 1,1'-dihydrocarbylsilanediyl-bridged metallocene is hafnium.

28. A process of converting meso chiral metallocene to racemic chiral metallocene, which process comprises contacting in a liquid organic medium, (i) meso metallocene of a transition, lanthanide or actinide metal in whatever chemical form and composition said meso metallocene exists when in said medium, and (ii) a Group 1 or 2 metal halide isomerization catalyst in whatever chemical form and composition said metal halide isomerization catalyst exists when in said medium, and supplying sufficient heat energy to said medium such that at least 10% of said meso metallocene is isomerized to the racemic metallocene.

29. A process according to claim 28 wherein (i) is a mixture of meso and racemic isomers of said metallocene in whatever chemical form(s) and composition(s) such mixture exists when in said medium.

30. A process according to claim 28 wherein the organic medium is an ether-containing medium, wherein (i) is a Group 4 metallocene, and wherein (ii) is lithium chloride or lithium bromide.

* * * * *